US005457066A

United States Patent [19]
Frank et al.

[11] Patent Number: 5,457,066
[45] Date of Patent: Oct. 10, 1995

[54] PROCESS FOR TRANSFORMING A HUMAN INSULIN PRECURSOR TO HUMAN INSULIN

[75] Inventors: Bruce H. Frank; Walker E. Prouty, both of Indianapolis; Richard E. Heiney, Greenwood; Mark R. Walden, Indianapolis, all of Ind.

[73] Assignee: Eli Lilly and Company, Indianapolis, Ind.

[21] Appl. No.: 882,189

[22] Filed: May 11, 1992

Related U.S. Application Data

[63] Continuation of Ser. No. 917,939, Oct. 14, 1986, abandoned.

[51] Int. Cl.[6] .................. C07K 14/62; C07K 14/625; C12P 21/06
[52] U.S. Cl. .................. 435/68.1; 530/303; 530/304; 530/305
[58] Field of Search .................. 435/68, 71, 272, 435/212, 213; 530/303, 304, 305

OTHER PUBLICATIONS

Steiner et al., Fed. Proc., 33(10):2105–2115 (1974).
Emdin et al., Diabetologia, 19:174–182 (1980).
A. L. Lehninger, Biochemistry, 819 (2nd ed., 3d printing 1977).
Kemmler, W., Peterson, J. D., and Steiner, D. F., J. Biol. Chem. 246, 6786–6791 (1971).
Yip, C. C., Proc. Nat. Acad. Sci. USA, 68, 1312–1315 (1971).
Grant, P. T., Coombs, T. L., and Frank, B. H., Biochem. J. 126, 433—440 (1972).
Chance, R. E., Diabetes 21, 461–467 (1972).
Emdin, S. O., Dodson, G. G., Cutfield, J. M., and Cutfield, S. M., Diabetologia 19, 174–182 (1980).
Sudmeier, J. L., Bell, S. J., Storm, M. C., and Dunn, M. F., Science 212, 560–562 (1981).
Given et al., J. Clin. Invest., 76, 1398–1405 (1985).
Frank et al., Biochem. Biophys., 38, 284–289 (1970).
Frank et al., Biochem., 11, 4926–4931 (1972).
Kemmler, Clark, and Steiner, Fed. Proc., 30, 1210 (1971).
Frank et al., Peptides: Synthesis, Structure, Function, 729–738 (1981).

*Primary Examiner*—Irene Marx
*Attorney, Agent, or Firm*—Steven P. Caltrider; James P. Leeds

[57] ABSTRACT

This specification describes a process for converting a human insulin precursor to human insulin, which comprises treating such human insulin precursor with trypsin and carboxypeptidase B in an aqueous medium containing per mole of human insulin precursor from about 0.1 to about 10 moles of one or more metal ions of those metals having Atomic Numbers 21 to 34, 39 to 52, 57 to 84, and 89 to 92.

10 Claims, No Drawings

PROCESS FOR TRANSFORMING A HUMAN INSULIN PRECURSOR TO HUMAN INSULIN

This application is a continuation, of application Ser. No. 06/917,939, now abandoned, filed Oct. 14, 1986.

BACKGROUND OF THE INVENTION

The ability to convert proinsulin to insulin using trypsin and carboxypeptidase B has been recognized for several years [see, e.g., Kemmler, W., Clark, J. L., Borg, J. and Steiner, D. F., *Fed. Proc.* 30 (1971) 1210; Kemmler, W., Peterson, J. D., and Steiner, D. F., *J. Biol. Chem.*, 246 (1971) 6786–6791]. An ongoing difficulty with this conversion methodology has been and continues to be the presence of substantially large amounts of difficultly-removable by-products in the reaction mixture. Specifically, in the conversion of human pro-insulin to human insulin, a large amount (about 4–6%) of Des-Thr(B30) human insulin is formed. This by-product, differing from human insulin by the absence of a single terminal amino acid, is, if capable of being separated from the product mixture at all, separated only by difficult and cumbersome methodology.

With the advent of recombinant DNA technology, for the first time large amounts of human proinsulin have become a reality. In using the human proinsulin as an intermediate in the production of insulin, a solution to the Des-Thr(B30)-hI impurity problem has become mandatory. Either one could seek ways to achieve purification of the human insulin from the contaminating Des-Thr(B30)-hI or seek a conversion process, the conditions of which minimize formation of the latter. It is to a new process for converting a human insulin precursor to human insulin with minimal formation of Des-Thr(B30)-hI that the present invention is directed.

SUMMARY OF THE INVENTION

Thus, this invention is directed to a process for converting a human insulin precursor to human insulin, such precursor having the formula

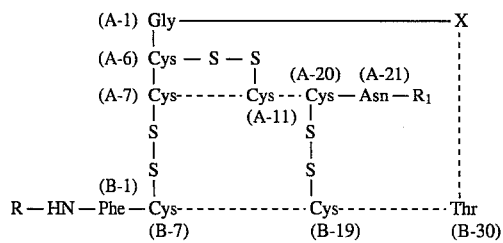

in which R is hydrogen, a chemically or enzymatically cleavable amino acid residue, or a chemically or enzymatically clearable peptide moiety having at least two amino acid residues;

$R_1$ is OH, Arg-Y, or Lys-Y in which Y is OH, an amino acid residue, or a peptide moiety having at least two amino acid residues; the moiety from A-1 to A-21 is the human insulin A-chain; the moiety from B-1 to B-30 is the human insulin B-chain; and X is a moiety which is joined to the insulin A-chain at the amino group of A-1 and to the insulin B-chain at the carboxyl group of B-30, which moiety can be enzymatically cleaved from and without disruption of both the A-chain and the B-chain, which comprises treating such human insulin precursor with trypsin and carboxypeptidase B in an aqueous medium containing per mole of human insulin precursor from about 0.1 to about 10 moles of one or more metal ions of those metals having Atomic Numbers 21 to 34, 39 to 52, 57 to 84, and 89 to 92.

DETAILED DESCRIPTION OF THE INVENTION

As indicated, the process of this invention represents an enhancement of the recognized conversion of proinsulin to insulin using trypsin and carboxypeptidase B. The process is applied to human insulin precursors of the foregoing formula, the most preferred of which is human proinsulin itself.

As used herein, the term "human insulin precursor" refers to a molecule which (1) contains the human insulin A-chain and the human insulin B-chain, (2) has at least three disulfide bonds represented by a joining of the sulfurs of each of the Cys moieties located in the A- and B-chains at (a) A-6 and A-11, (b) A-7 and B-7, and (c) A-20 and B-19, respectively, and (3) has a removable connecting moiety which is joined to the insulin A-chain at the amino group of A-1 and to the insulin B-chain at the carboxyl group of B-30.

The group R is hydrogen, an amino acid residue, or a peptide moiety having at least two amino acid residues. In those instances in which R is an amino acid residue or a peptide moiety, R is a group which is cleavable from the insulin precursor product without loss of the integrity of the residual insulin structure. Any of a wide variety of amino acid residues or peptide moieties qualify within the definition of the group R. Examples of clearable amino acid residues are basic amino acids such as arginine (Arg) or lysine (Lys) as well as peptide moieties terminating at the carboxyl by such amino acid residues. These are recognized as susceptible to cleavage upon treatment with the proteolytic enzyme trypsin. Another example of a cleavable amino acid residue is methionine (Met) as well, again, as a peptide moiety having Met at its carboxy terminal. These can be removed by treatment with cyanogen bromide. A further example is tryptophan (Trp) or a peptide moiety containing Trp at its carboxy terminal. This is removed upon treatment with N-bromosuccinimide.

The group $R_1$ is hydroxyl, arginine, lysine, or a peptide having arginine or lysine at its amino terminus. When $R_1$ is arginine, lysine, or a peptide having either of these residues at its amino terminus, the amino acid or peptide will be cleaved under the conditions of the process of this invention with formation of a product in which $R_1$ is hydroxyl.

The connecting moiety, X, of the insulin precursor can be any of a wide range of structures. Preferably, the moiety X is a polypeptide. The polypeptide generally has at least 2 and preferably from about 2 to about 35 and most preferably from about 6 to about 35 amino acid residues. The moiety X is joined to the A-chain at the amino group of A-1 and to the B-chain at the carboxyl group of B-30. Most preferably, the connecting moiety, X, when it is a peptide, is the natural connecting peptide of human proinsulin, such connecting peptide having the formula:

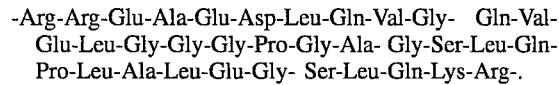
-Arg-Arg-Glu-Ala-Glu-Asp-Leu-Gln-Val-Gly- Gln-Val-Glu-Leu-Gly-Gly-Gly-Pro-Gly-Ala- Gly-Ser-Leu-Gln-Pro-Leu-Ala-Leu-Glu-Gly- Ser-Leu-Gln-Lys-Arg-.

Although it is preferred to use the natural connecting sequence, as indicated above, much shorter peptide sequences can be used for the connecting peptide. The only requirements are (1) that they be of sufficient length to permit proper disulfide bond formation between the A- and B-chains, and (2) that they be cleavable from the insulin precursor with accompanying insulin formation. A typical dipeptide which can be used is -Arg-Arg-. In addition, modifications of the foregoing dipeptide having the formula -Arg-X'-Arg- in which X' represents at least one amino acid residue can be readily employed. Highly preferred connecting peptides are -Arg-Arg-Lys-Arg- as well as longer chain peptides having the structure -Arg-Arg-$X^2$-Lys-Arg- in which $X^2$ is at least one amino acid residue and preferably at least two amino acid residues. These latter, of course, include the natural connecting peptide.

The process of this invention is conducted in an aqueous medium. The term "aqueous medium" requires the presence of water; it does not, however, preclude the presence of water-miscible organic solvents such as methanol, ethanol, acetone, N,N-dimethylformamide, and the like. The human insulin precursor is present in the medium at a concentration of up to about 20 mM. Preferably, the human insulin precursor concentration is substantially lower, ranging generally from about 0.1 mM to about 10 mM; more preferably, from about 0.5 to about 5 mM; and most preferably, from about 1 to about 3 mM.

The conversion is carried out at any of a wide range of temperatures, generally from about 0° C. to about 40° C. Preferably, the reaction is conducted at a temperature of from about 4° C. to about 25° C., and, most preferably, from about 10° C. to about 15° C.

The pH of the reaction mixture can range anywhere from about 4 to about 12. However, best results are obtained by careful pH control such that the reaction is conducted at a pH in the range of from about 6 to about 9, preferably from about 7 to about 8, and, when precisely controlled, from about 7.2 to about 7.6.

pH Control generally is assisted by the use of a buffering agent. Any of a wide range of typical buffers can be employed. Examples of suitable buffers are TRIS, ethylene diamine, triethanolamine, glycine, HEPES (N-2-hydroxyethylpiperazine-$N^1$-2-ethanesulfonic acid), and the like.

The amount of trypsin and carboxypeptidase B that generally is used is related both as between the two enzymes and to the amount of human insulin precursor. The enzymes can be incorporated in the reaction mixture either in solution or, using recognized techniques, can be immobilized on a suitable support and thereby made available in the reaction medium.

On a weight:weight basis, carboxypeptidase B generally will be present in an amount relative to the human insulin precursor of from about 1:10 to about 1:5,000; preferably, from about 1:500 to about 1:3,500; and, most preferably, from about 1:1,000 to about 1:3,000.

On a weight:weight basis, trypsin generally will be present in an amount relative to the human insulin precursor of from about 1:20 to about 1:250,000; preferably, from about 1:300 to about 1:20,000; and, most preferably, from about 1:5,000 to about 1:15,000.

The ratio of carboxypeptidase B to trypsin in the reaction mixture also represents an important parameter. Generally, on a weight basis, the ratio, carboxypeptidase B to trypsin, will be from about 1:1 to about 10:1, and, preferably, from about 2:1 to about 5:1.

The key discovery which forms the basis of this invention resides in the finding that the presence of a defined amount of one or more of a wide range of metal ions substantially diminishes the amount of Des-Thr(B30)-hI formed during the reaction.

Although certain metal ions are highly preferred, it has been discovered that a wide range of such ions are useful. Metal ions that can be employed are those of the following metals: scandium (Sc), titanium (Ti), vanadium (V), chromium (Cr), manganese (Mn), iron (Fe), cobalt (Co), nickel (Ni), copper (Cu), zinc (Zn), gallium (Ga), germanium (Ge), arsenic (As), selenium (Se), yttrium (Y), zirconium (Zr), niobium (Nb), molybdenum (Mo), technetium (Tc), ruthenium (Ru), rhodium (Rh), palladium (Pd), silver (Ag), cadmium (Cd), indium (In), tin (Sn), antimony (Sb), tellurium (Te), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutecium (Lu), hafnium (Hf), tantalum (Ta), tungsten (W), rhenium (Re), osmium (Os), iridium (Ir), platinum (Pt), gold (Au), mercury (Hg), thallium (Tl), lead (Pb), bismuth (Bi), polonium (Po), actinium (Ac), thorium (Th), protactinium (Pa), and uranium (U).

Although ions of any of the foregoing metals can be used in the process of this invention, highly preferred subclasses of narrowing scope and thus increased preference are as follows:

(1) chromium, molybdenum, tungsten, mercury, antimony, bismuth, nickel, iron, cobalt, zinc, cadmium, copper, tin, lead, europium, uranium, platinum, and manganese.

(2) nickel, iron, cobalt, zinc, cadmium, copper, tin, lead, europium, uranium, platinum, and manganese.

(3) nickel, zinc, cobalt, and cadmium.

(4) nickel and zinc.

(5) nickel.

In accordance with the process of this invention, ions of one or more of the foregoing metals are added to the human insulin precursor reaction mixture. The amount of ion from the foregoing metals in the aggregate present in the reaction mixture ranges from about 0.1 to about 10 moles per mole of human insulin precursor. The actual amount used preferably is at the lower end of the foregoing range, generally being from about 0.1 to about 2 moles per mole of human insulin precursor. Most preferably, the amount is from about 0.3 to about 1 mole per mole of human insulin precursor, and, ideally, from about 0.33 to about 0.6 moles per mole of human insulin precursor.

The conversion reaction normally is conducted for a period of from about 2 hours to about 48 hours, usually from about 8 hours to about 16 hours. The reaction can be monitored by high performance liquid chromatography, and the time of reaction carefully coordinated with human insulin production.

Another facet of this invention, wholly unexpected, is the finding that the amount of Des-Thr(B30)-hI production can be further diminished by incorporation in the reaction mixture of one or more metal ions from another class of metals. This further improvement is particularly evident when the amount of the first metal ion is in the range of from about 0.1 mole to about 0.6 mole per mole of human insulin precursor. It is highly advantageous to add an amount of a metal ion of a metal selected from the group consisting of beryllium (Be), magnesium (Mg), calcium (Ca), strontium (Sr), barium (Ba), and radium (Ra). Preferably the ion will be that of calcium, barium, strontium, or magnesium, and, most preferably, will be that of calcium.

The amount of the second metal ion will range from about 0.5 mole to about 5 moles per mole of the human insulin precursor and, preferably, from about 1 mole to about 3 moles per mole of the human insulin precursor.

What has been most surprising about the use of a second metal ion as described in the foregoing is the fact that an ion of the second class, specifically calcium, is known to stabilize trypsin and when it is used in the absence of an ion of a metal of the first class, it has been noted that the production of DesThr(B30)-hI is actually increased.

Typically, the process of this invention is carried out by dissolving the human insulin precursor in an aqueous medium. The final mixture will generally be at a concentration of about 1 mM to about 3 mM and have a pH of about 8. Ion of a metal of the second class (if used) is then added. Typically, $CaCl_2$ will be added to a concentration of about 5 mM when the foregoing concentration of the human insulin precursor is used. An ion of a metal of the first class, typically Ni(II), is then added to a concentration of about 0.5 moles per mole of the human insulin precursor. The pH of the mixture is adjusted to 7.3–7.5, and carboxypeptidase B (about 1:2,500 w/w human insulin precursor) is added followed by trypsin (about 1:12,500 w/w human insulin precursor). The reaction is allowed to proceed, the mixture being maintained at about 12° C. Progress of the reaction is carefully monitored by high performance liquid chromatography.

The following examples are provided to demonstrate the efficacy of the process of this invention. They are not intended to be limiting upon the broad scope thereof.

EXAMPLE 1

Effect of Varying Trypsin and Carboxypeptidase B Concentrations.

Human proinsulin (hPI) was dissolved in 20 mM ethylene diamine (EDA) buffer, pH 7.0, at a concentration of 10.85 g/liter. The mixture was divided into two portions. To the first portion, porcine pancreatic carboxypeptidase B (CpB) was added to a final concentration of 3.74 mg/liter. This solution was divided into six one-milliliter aliquots, and bovine pancreatic trypsin, previously treated with tosylphenylalanyl chloromethyl ketone (trypsin-TPCK) was added at 1.0, 1.4, 1.8, 2.8, 3.6, and 5.4 mg/liter, respectively. Each of the samples was incubated for 8 hours at 23° C. The Des-Thr(B30)-hI levels were determined by High Pressure Liquid Chromatography (HPLC) and are shown in Table 1.

The second portion of the hPI solution was divided into five one-milliliter aliquots. CpB was added to a concentration of 1.1, 1.5, 2.2, 3.7, and 5.4 mg/liter, respectively. Trypsin-TPCK then was added to each aliquot to a concentration of 2.71 mg/liter. Each of the samples was incubated for 8 hours at 23° C. The results are presented in Table 2.

In both Tables 1 and 2, the amount of Des-Thr(B30)-hI is expressed as a percent of hi as determined by HPLC. As the data demonstrate, at fixed levels of CpB, Des-Thr(B30)-hI is reduced by decreasing levels of trypsin. Conversely, at fixed levels of trypsin, increasing levels of CpB lead to decreased levels of Des-Thr(B30)-hI.

TABLE 1

Effect of Increasing Levels of Trypsin on hPI Transformation

| CpB, mg/liter | Trypsin, mg/liter | % Des-Thr(B30)-hI as % of hI |
|---|---|---|
| 3.7 | 1.0 | 2.4 |
| 3.7 | 1.4 | 2.6 |
| 3.7 | 1.8 | 2.7 |
| 3.7 | 2.8 | 3.3 |
| 3.7 | 3.6 | 3.9 |
| 3.7 | 5.4 | 5.1 |

TABLE 2

Effect of Increasing Levels of CpB on hPI Transformation

| CpB, mg/liter | Trypsin, mg/liter | % Des-Thr(B30)-hI as % of hI |
|---|---|---|
| 1.1 | 2.71 | 4.8 |
| 1.5 | 2.71 | 4.0 |
| 2.2 | 2.71 | 4.1 |
| 3.7 | 2.71 | 3.4 |
| 5.4 | 2.71 | 2.6 |

EXAMPLE 2

Effect of Temperature on Des-Thr(B30)-hI Production.

hPI (60 mg) was dissolved in 20 mM ethylene diamine (6.0 ml), pH 7.5–8.0. Porcine carboxypeptidase B and bovine trypsin-TPCK were added sequentially to provide a substrate (hPI):enzyme ratio of 5000:1:1, w/w, for hPI:CpB:trypsin-TPCK. Two milliliter aliquots were incubated at 12, 24, and 37° C. for the lengths of time necessary to achieve maximum hi yield as measured by HPLC, i.e., 14, 6, and 4 hours, respectively. As shown in the results in Table 3, lower temperatures favored lower Des-Thr(B30)-hI formation.

TABLE 3

Temperature Effect

| Incubation Temperature, °C. | % Des-Thr(B30)-hI as % hI |
|---|---|
| 12 | 4.4 |
| 24 | >7 |
| 37 | >9 |

EXAMPLE 3

Effect of Metals on Derivative Formation.

hPI (360 mg) was dissolved in 20 ml of 20 mM glycine, pH 7.65. The solution was divided into two 10.0 ml aliquots, and calcium ion at 5 mM was added to one aliquot. Each aliquot was divided further into three portions. A portion from the calcium ion-containing and one from the calcium ion-free aliquots then were treated as follows: For one set, zinc ion was added to give a 0.33 molar ratio relative to hPI. To another set, nickel ion was added to give a 0.36 molar ratio relative to hPI. Enzymes were added to all mixtures to provide the following weight ratios: hPI:CpB:trypsin-TPCK::13,500:5:1. The pH of each of the mixtures was adjusted to 7.65–7.7 and incubated at 12° C. for 16 hours. The results, shown in Table 4, illustrate the effect of nickel and zinc in reducing the level of Des-Thr(B30)-hI formation. They further illustrate the enhancement of this effect by calcium.

TABLE 4

Effect of Metals on hPI Transformation

| Metal Ion | Des-Thr(B30)-hI, as % hI |
|---|---|
| None | 4.0 |
| Ca | 7.6 |
| Zn | 1.6 |
| Ni | 1.7 |

TABLE 4-continued

Effect of Metals on hPI Transformation

| Metal Ion | Des-Thr(B30)-hI, as % hI |
|---|---|
| Zn + Ca | 0.7 |
| Ni + Ca | <0.2[1] |

[1]Assay was less than detectable limit which was 0.20% of hI.

EXAMPLE 4

Effect of Varying Ni(II) Concentration on Derivative Formation in the hPI Conversion Reaction.

hPI (245 mg) was dissolved in 12.0 ml of 50 mM glycine, pH 7.4. Calcium ion was added from a 1 M CaCl$_2$ stock solution to yield a final Ca(II) concentration of 5 mM. Nickel(II) from a 0.11 M NiCl$_2$ stock solution was added to 2 ml aliquots to give one sample each of a molar ratio to hPI of 0, 0.24, 0.37, 0.44, 0.51 and 0.58. CpB was added to each tube to yield 7.4 μg/ml (4.87 mg/ml stock) followed by addition of trypsin-TPCK to yield a final concentration of 2.96 μg/ml (1.0 mg/ml stock solution). The pH of all samples was adjusted to 7.40, and each was incubated at 12° C. Reactions were stopped after 12 hours, and levels of Des-Thr(B30)-hI and hI were measured. The results shown in Table 5, indicate that increased levels of nickel resulted in reduced production of Des-Thr(B30)-hI.

TABLE 5

Effect of Varying NI(II) Concentration

| Molar Ratio, Ni(II)/hPI | % Des-Thr(B30)-hI, as % hI |
|---|---|
| 0 | 7.6 |
| 0.24 | 1.9 |
| 0.37 | 0.61 |
| 0.44 | 0.72 |
| 0.51 | 0.33 |
| 0.58 | 0.28 |

EXAMPLE 5

Effect of Various Metal Cations on Derivative Formation in the hPI Conversion Reaction.

hPI (936 mg) was dissolved in 36 ml of 5 mM glycine, and the pH was adjusted to 7.8-8.0. Calcium ion was added as CaCl$_2$ (1 M stock) to 5 mM. Aliquots of 3 ml each were removed, and various metal ions were added at the concentration shown in Table 6. After equilibration at 12° C., enzymes were added to provide weight ratios as follows: hPI:CpB:trypsin-TPCK::13,500:5:1.

The samples were incubated at 12° C. for 13 hours, and measured for hi and Des-Thr(B30)-hI. The results shown in Table 6 indicate that any of a wide range of metal ions are effective in reducing the production of Des-Thr(B30)-hI.

TABLE 6

Effect of Various Divalent Cations

| Divalent Metal Ion | Molar Ratio, M(II)/hPI | % Des-Thr(B30)-hI as % of hI |
|---|---|---|
| Zn | 0.3 | 1.02 |
| Zn | 0.5 | 0.78 |
| Ni | 0.22 | 2.29 |
| Ni | 0.37 | 0.72 |
| Co | 0.26 | 2.35 |
| Co | 0.43 | 0.89 |
| Cd | 0.19 | 1.63 |
| Cd | 0.31 | 0.88 |
| Cu | 0.14 | 3.23 |
| Cu | 0.23 | 1.34 |

EXAMPLE 6

Large Scale Transformation of hPI Using Ni(II) and Ca(II).

hPI (448.5 g), dissolved in 15 mM glycine buffer, pH 7.4 (33.0 L), was cooled and maintained at 12° C. Calcium(II) was added to 5 mM by addition of 1.0 M CaCl$_2$ stock solution (0.165 L). After stirring 10 minutes, nickel(II) was added to give a molar ratio Ni(II):hPI of 0.44:1 by addition of solid NiCl$_2$·6H$_2$O (5.0 g). The solution was stirred gently another 10 minutes, and CpB (36.8 ml, 179.4 mg) was added from a 4.87 mg/ml stock solution. Trypsin-TPCK (35.9 ml, 35.9 mg) then was added from a 1.0 mg/ml stock solution. The reaction reached completion in 10 hours as measured by maximal production of hi. At harvest, the mixture contained about 0.29% Des-Thr(B30)-hI, which approaches the detection limit of the method of detection of this compound.

We claim:

1. A process for converting a human insulin precursor to human insulin, such precursor having the formula

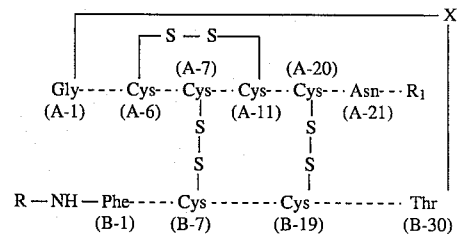

where R is hydrogen, a chemically or enzymatically clearable amino acid residue, or a chemically or enzymatically cleavable peptide moiety having at least two amino acid residues;

R$_1$ is OH, Arg-Y, or Lys-Y in which Y is OH, an amino acid residue, or a peptide moiety having at least two amino acid residues;

the moiety from A-1 to A-21 is the human insulin chain; the moiety from B-1 to B-30 is the human insulin B-chain; and X is a polypeptide moiety which is joined to the insulin A-chain at the amino group of A-1 and to the insulin B-chain at the carboxyl group of B-30, which moiety can be enzymatically cleaved from and without disruption of both the A-chain and the B-chain;

which comprises treating such human insulin precursor with trypsin and carboxypeptidase B in an aqueous medium containing per mole of human insulin precursor from about 0.1 to about 2 moles of nickel ions, such that the amount of des-Thr(B30)-human insulin produced is less than 2.4% relative to human insulin;

provided that the human insulin precursor is present in the aqueous medium at a concentration of up to about 20 mM;

further provided that carboxypeptidase B is present in an amount on a weight basis relative to the human insulin precursor, from about 1:10 to about 1:5,000;

further provided that trypsin is present in an amount on a weight basis, relative to the human insulin precursor, from about 1:20 to about 1:250,000; and further provided that the weight ratio of carboxypeptidase B to trypsin is from about 1:1 to about 10:1.

2. A process for converting a human insulin precursor to human insulin, such precursor having the formula

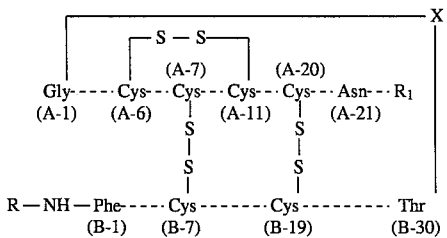

where R is hydrogen, a chemically or enzymatically cleavable amino acid residue, or a chemically or enzymatically cleavable peptide moiety having at least two amino acid residues;

$R_1$ is OH, Arg-Y, or LyS-Y in which Y is OH, an amino acid residue, or a peptide moiety having at least two amino acid residues;

the moiety from A-1 to A-21 is the human insulin A-chain; the moiety from B-1 to B-30 is the human insulin B-chain; and x is a polypeptide moiety which is joined to the insulin A-chain at the amino group of A-1 and to the insulin B-chain at the carboxyl group of B-30, which moiety can be enzymatically cleaved from and without disruption of both the A-chain and the B-chain;

which comprises treating such human insulin precursor with trypsin and carboxypeptidase B in an aqueous medium containing per mole of human insulin precursor from about 0.1 to about 2 moles of one or more metal ions of a metal selected from the group consisting of nickel, zinc, cobalt, and cadmium; and a second metal ion of a metal selected from the group consisting of beryllium, magnesium, calcium, strontium, barium, and radium; such that the amount of des-Thr (B3.0)-human insulin produced is less than 2.4% relative human insulin;

provided that the concentration of the second metal ion is from about 0.5 mole to about 5 moles per mole of the human insulin precursor;

further provided that the human insulin precursor is present in the aqueous medium at a concentration of up to about 20 mM:

further provided that carboxypeptidase B is present in an amount on a weight basis, relative to the human insulin precursor, from about 1:10 to about 1:5,000;

further provided that trypsin is present in an amount on a weight basis, relative to the human insulin precursor, from about 1:20 to about 1:250,000.

3. Process of claim 2, in which the second metal ion is that of a metal selected from the group consisting of calcium, barium, strontium, and magnesium.

4. Process of claim 3, in which the second metal ion is calcium ion.

5. Process of claim 4, in which the second metal ion is present in an amount of from about 1 mole to about 3 moles per mole of the human insulin precursor.

6. Process of claim 5, in which the human insulin precursor is human proinsulin.

7. A process for converting a human insulin precursor to human insulin, such precursor having the formula

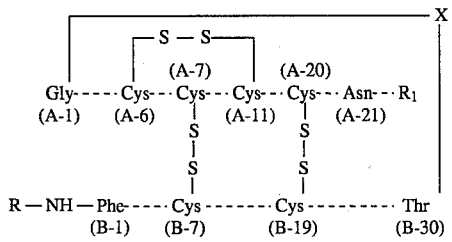

where R is hydrogen, a chemically or enzymatically cleavable amino acid residue, or a chemically or enzymatically cleavable peptide moiety having at least two amino acid residues:

$R_1$ is OH, Arg-Y, or Lys-Y in which Y is OH, an amino acid residue, or a peptide moiety having at least two amino acid residues;

the moiety from A-1 to A-21 is the human insulin A-chain: the moiety from B-1 to B-30 is the human insulin B-chain; and X is a polypeptide moiety which is joined to the insulin A-chain at the amino group of A-1 and to the insulin B-chain at the carboxyl group of B-30, which moiety can be enzymatically cleaved from and without disruption of both the A-chain and the B-chain;

which comprises treating such human insulin precursor with trypsin and carboxypeptidase B in an aqueous medium containing per mole of human insulin precursor from about 0.1 to about 10 moles of nickel ions, such that the amount of des-Thr(B30)-human insulin produced is less than 2.4% relative to human insulin.

8. A process for converting a human insulin precursor to human insulin, such precursor having the formula

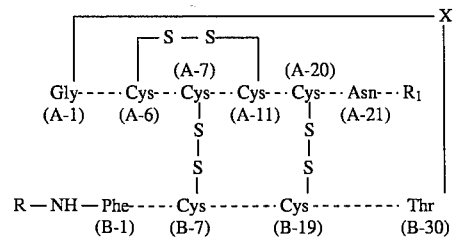

where R is hydrogen, a chemically or enzymatically cleavable amino acid residue, or a chemically or enzymatically clearable peptide moiety having at least two amino acid residues;

$R_1$ is OH, Arg-Y, or Lys-Y in which Y is OH, an amino acid residue, or a peptide moiety having at least two amino acid residues;

the moiety from A-1 to A-21 is the human insulin A-chain; the moiety from B-1 to B-30 is the human insulin B-chain; and X is a polypeptide moiety which is joined to the insulin A-chain at the amino group of A-1 and to the insulin B-chain at the carboxyl group of B-30, which moiety can be enzymatically cleaved from and without disruption of both the A-chain and the B-chain;

which comprises treating such human insulin precursor with trypsin and carboxypeptidase B in an aqueous medium containing per mole of human insulin from about 0.1 to about 2 moles of one or more metal ions of a metal selected from the group consisting of nickel, zinc, cobalt, and cadmium: and a second metal ion of a metal selected from the group consisting of beryllium, magnesium, calcium, strontium, barium, and radium; such that the amount of des-Thr(B30)-human insulin produced is less than 2.4% relative to human insulin;

provided that the concentration of the second metal ion is from about 0.5 mole to about 5 moles per mole of the human insulin precursor.

9. The process of claim 8, wherein the second met ion is that of a metal selected from a group consisting of calcium, barium, strontium, and magnesium.

10. The process of claim 9, wherein the second metal ion is calcium ion.

* * * * *

UNITED STATES PATENT AND TRADEMARK OFFICE
CERTIFICATE OF CORRECTION

PATENT NO.  : 5,457,066

DATED       : October 10, 1995

INVENTOR(S) : B. Frank et al.

It is certified that an error appears in the above-identified patent and that said Letters Patent is hereby corrected as shown below:

Column 8, line 52 (Claim 1, line 5), delete "clearable" and insert --cleavable-- therefor.

Column 8, line 58 (Claim 1, line 11), delete "insulin chain" and insert --insulin A-chain-- therefor.

Column 9, line 36 (Claim 2, line 8), delete "LyS-Y" and insert --Lys-Y-- therefor.

Column 9, line 42 (Claim 2, line 14), delete "x is a" and insert --X is a-- therefor.

Column 9, line 56 (Claim 2, line 28), delete "B3.0" and insert --B30-- therefor.

Column 9, line 57 (Claim 2, line 29), following "relative" insert --to--.

Column 9, line 67 (Claim 2, line 38), following "1:5,000;" insert --and--.

Column 10, line 38 (Claim 7, line 14), delete "joined to the insulin" and insert --joined to the human insulin-- therefor.

Column 10, line 39 (Claim 7, line 15), delete "amino group" and insert --amino acid group-- therefor.

UNITED STATES PATENT AND TRADEMARK OFFICE
CERTIFICATE OF CORRECTION

PATENT NO. : 5,457,066
DATED : October 10, 1995
INVENTOR(S) : B. Frank, et. al.

It is certified that error appears in the above-indentified patent and that said Letters Patent is hereby corrected as shown below:

Column 11, line 6 (claim 8, line 14), delete "joined to the insulin" and insert--joined to the human insulin-- therefor.

Column 11, line 10 (claim 8, line 18), delete "the B-chain" and insert --B-chain -- therefor.

Column 12, line 10 (claim 9, line 1), delete "met" and insert--metal--therefor

Signed and Sealed this

Eleventh Day of March, 1997

Attest:

BRUCE LEHMAN

Attesting Officer     Commissioner of Patents and Trademarks